(12) United States Patent
Wolf et al.

(10) Patent No.: US 8,262,878 B2
(45) Date of Patent: *Sep. 11, 2012

(54) CONTROLLED ACTIVATION PH SENSOR

(75) Inventors: Erich H. Wolf, San Diego, CA (US);
Charles Bankert, San Diego, CA (US);
Ross Tsukashima, San Diego, CA (US);
Elmer Custodio, San Diego, CA (US)

(73) Assignee: Sierra Medical Technology, Inc., San Diego, CA (US)

( * ) Notice: Subject to any disclaimer, the term of this patent is extended or adjusted under 35 U.S.C. 154(b) by 1028 days.

This patent is subject to a terminal disclaimer.

(21) Appl. No.: 11/881,021

(22) Filed: Jul. 25, 2007

(65) Prior Publication Data

US 2009/0026078 A1  Jan. 29, 2009

(51) Int. Cl.
*G01N 27/414* (2006.01)

(52) U.S. Cl. ........ 204/433; 204/402; 204/416; 600/361; 436/68

(58) Field of Classification Search .............. 205/787.5; 204/402, 416, 433; 600/529, 361, 547; 436/68
See application file for complete search history.

(56) References Cited

U.S. PATENT DOCUMENTS

| 4,062,750 | A  | * | 12/1977 | Butler | 257/253 |
|---|---|---|---|---|---|
| 5,354,449 | A  | * | 10/1994 | Band et al. | 204/433 |
| 7,166,201 | B2 | * | 1/2007  | Wolf | 204/433 |
| 7,238,267 | B2 | * | 7/2007  | Wolf et al. | 204/433 |
| 2003/0057108 | A1 | * | 3/2003 | Sridharan | 205/775 |
| 2005/0115833 | A1 | * | 6/2005 | Wolf et al. | 204/412 |
| 2005/0115834 | A1 | * | 6/2005 | Wolf | 204/416 |
| 2006/0270936 | A1 | * | 11/2006 | Tsukashima et al. | 600/481 |
| 2006/0270940 | A1 | * | 11/2006 | Tsukashima et al. | 600/529 |

* cited by examiner

*Primary Examiner* — J. Christopher Ball
(74) *Attorney, Agent, or Firm* — Michael Klicpera

(57) ABSTRACT

The present invention pertains to a means of combining and configuring specific hydrophilic and dielectric materials in such a way as to allow an antimony/reference electrode pH sensor to be packaged and stored dry yet become fully hydrated to an activated state after exposure to aqueous liquids. The sensor is packaged and stored dry to maintain component stability and minimize component degradation. When the user removes the sensor from the package and the sensor tip is submerged in a hydration (ion conduction) media or solution, the hydrophilic coating along with the impregnated reference wick, absorb the fluid to create an electrolytic gel inside the reference wick, which activates the pH sensor.

23 Claims, 3 Drawing Sheets

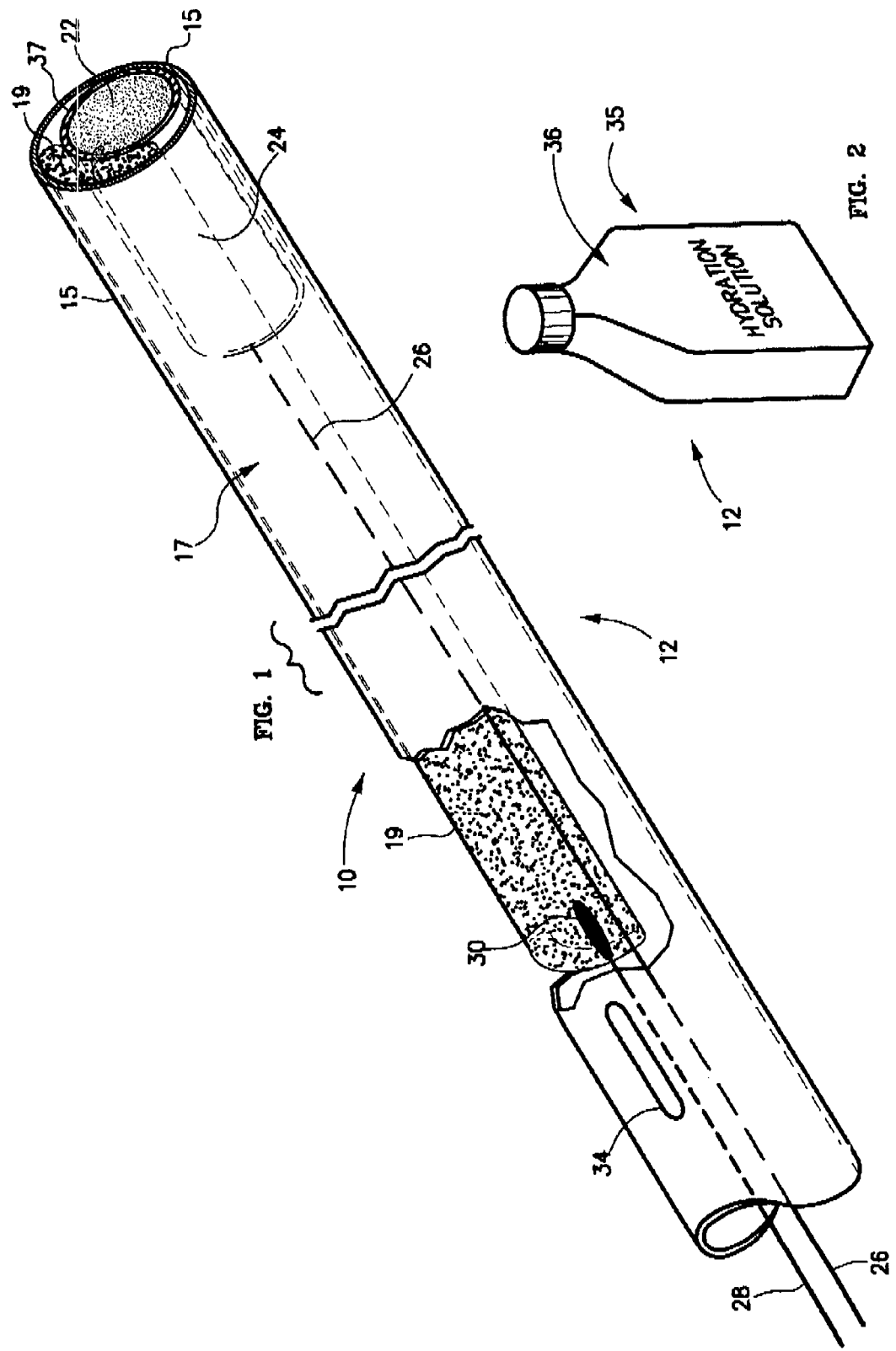

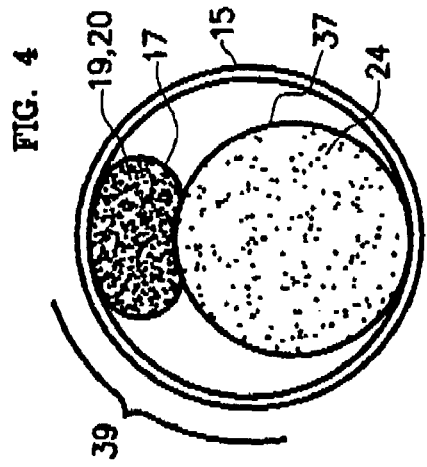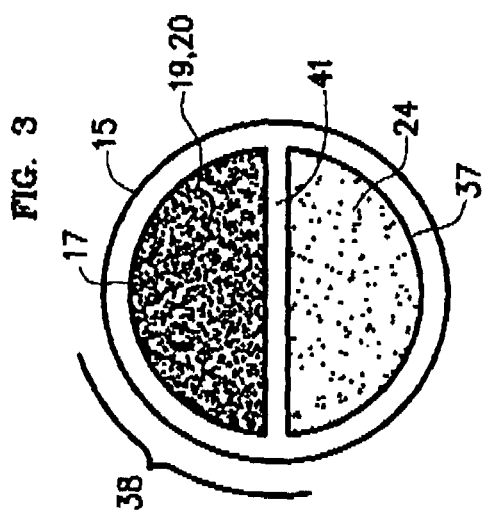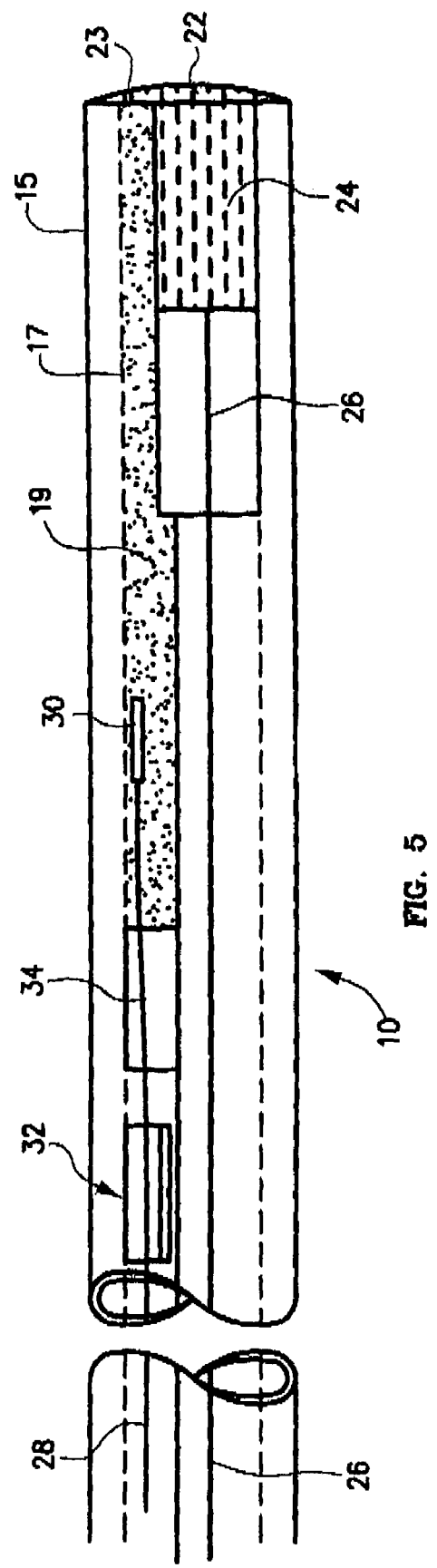

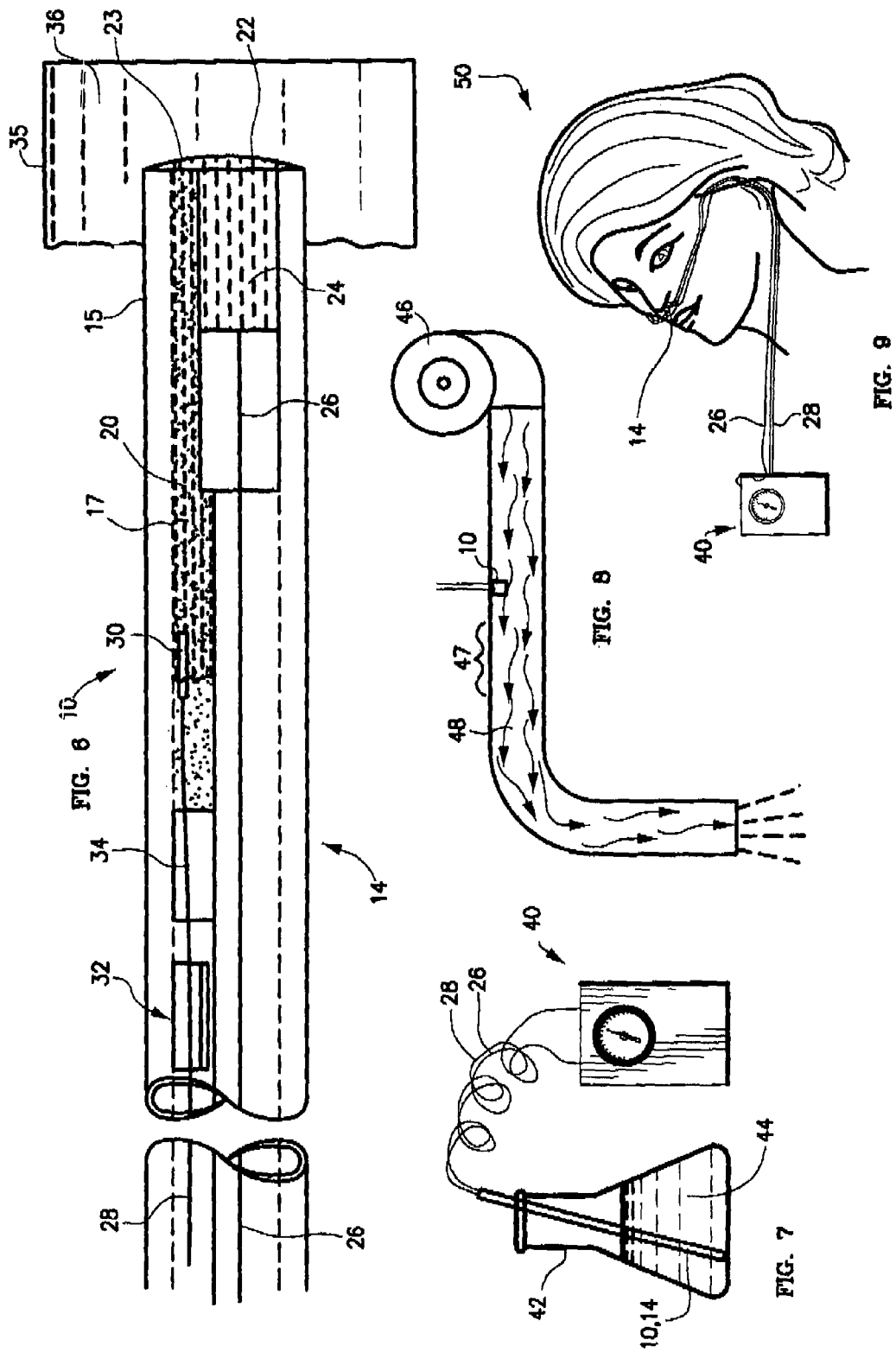

CONTROLLED ACTIVATION PH SENSOR

FIELD OF THE INVENTION

The art to which this invention relates is in the field of monitoring pH or other constituents. More specifically, an invention which utilizes a means of combining and configuring materials within a pH sensor that allows dry packaging and rapid hydration to attain an activated state.

BACKGROUND OF THE INVENTION

Since the inception of the modern pH scale, a variety of devices have been developed to monitor and interpret changes in the negative log of the concentration of hydrogen protons in a solution, "pH".

For general or industrial applications, pH papers or liquid indicators that change color as the pH level of a solution varies are used. These indicators are convenient to use, but have limitations on their accuracy, and can be difficult to interpret correctly in some conditions.

For laboratory applications, a more accurate tool is employed that relies on electronic pH measurement means. This equipment typically consists of three parts: a pH measuring electrode, a reference electrode, and a high input impedance meter. The pH measuring electrode and reference electrode can be thought of as a battery, with a voltage that varies with pH of the measured solution. The system can be made up of a large glass bulb with a hydrogen ion sensitive coating. This coating creates a millivolt output that varies with changes in relative hydrogen ion concentration inside and outside of the bulb. The reference electrode can consist of a combination of metals, chemicals, and liquid commonly known as electrolytic fluid or gel, that create a millivolt output that does not vary with changes in hydrogen ion concentration.

In medical applications where the environmental pH of the esophagus or pharyngeal regions need to be measured, a smaller, more compact sensor system is utilized. The pH sensing element usually consists of an exposed antimony metal segment, that changes voltage with the change in pH, and a silver/silver chloride reference electrode, that does not change voltage with the change in pH. The reference electrode of these pH sensors is usually protected from outside contaminants by nesting the element within the body of the pH sensor and surrounding it with ion conducting electrolytic gel. The reference wick, typically a strand of fibrous material, is used as a conduit between the ion conducting gel and the environment which is to be measured.

As moisture is necessary to maintain the ion conducting properties of the electrolytic gel, these esophageal or pharyngeal pH sensors must be packaged in a way as to retain sufficient moisture for ion conduction. Manufacturing a pH sensor that has a fluid element, as well as packaging to retain that moisture during shipping and storage, poses a number of challenges such as moisture retention, fluid migration, and component deterioration.

SUMMARY OF THE INVENTION

The present invention pertains to a means of combining and configuring specific hydrophilic and dielectric materials in such a way as to allow an antimony/reference electrode pH sensor to be packaged and stored dry yet become fully hydrated to an activated state after exposure to aqueous liquids.

The following drawings and specification detail the construction of the present invention. The distal section of the pH sensor shows an antimony metal segment that is encased in a dielectric material to maintain isolation from the reference electrode. Adjacent to the antimony is the reference wick, impregnated with a dry matrix of hygroscopic materials such as hydroxyethylcellulose and sodium chloride, which when hydrated, forms an electrolytic gel. The reference wick is sheathed with a polymer tube, which acts as a capillary tube, facilitating the liquid flow. An expansion plug at the proximal end of the tube regulates the amount of liquid absorbed and controls the electrolyte concentration. To initiate hydration and increase the wetability of the reference wick, a hydrophilic and/or hydroscopic coating is applied to the sensor tip.

The sensor is packaged and stored dry to maintain component stability and minimize component degradation. When the user removes the sensor from the package and the sensor tip is submerged in a hydration solution, the hydrophilic coating along with the impregnated reference wick, absorb the solution to create an electrolytic gel inside the reference wick, which activates the pH sensor. When the hydration solution contacts the reference element, the pH sensor is activated.

These and other features, aspects and advantages of the present invention will become better understood with reference to the following descriptions and claims.

BRIEF DESCRIPTION OF THE DRAWINGS

FIG. 1 is a partially sectional side view of the sensor apparatus kit demonstrating in detail the orientation and components of the pH sensing means.

FIG. 2 is a side view of a container filled with a hydration solution that is used to activate the sensor apparatus.

FIG. 3 is a top view of the terminal end of one embodiment of the sensor apparatus demonstrating the orientation of the reference wick separated by an inner bridge from the antimony metal segment in a multi-luminal design.

FIG. 4 is a top view of the terminal end of another embodiment of the sensor apparatus demonstrating the offset co-linear orientation of the antimony metal segment and the reference wick.

FIG. 5 is a sectional side view of the terminal end of another embodiment sensor apparatus demonstrating the orientation of the antimony metal segment and wire assembly that is electrically isolated from the reference element or electrode and reference wick in a dry state.

FIG. 6 is a sectional side view of the sensor apparatus demonstrating the orientation of the antimony metal segment and wire assembly which is electrically isolated from the reference sensor and reference wick whereby the sensor is activated by the controlled uptake of the hydration solution into the reference wick.

FIG. 7 is the present invention sensor being used in an example liquid environment.

FIG. 8 is the present invention sensor being used in an example humid gaseous environment.

FIG. 9 is the present invention sensor being used in an example clinical application.

DESCRIPTION OF THE PREFERRED EMBODIMENT

The present invention pertains to an apparatus that includes a controlled activation means in a sensor that can detect changes in pH levels of humidified gases and liquid samples. When electronically connected to a computerized or analog display means, sensitive quantitative measurements can be obtained. Given the construction of current pH devices available today, there is a need in the field for a novel, controlled activation pH probe that can be used in fluid or humidified gases.

FIG. 1 illustrates the present invention consisting of a sensor apparatus 10 comprised of several components. As shown in this Figure, a typical partially sectional side view of the sensor apparatus demonstrates the orientation and components of the pH sensor apparatus 10.

As shown by the combination of FIGS. 1 and 2, it is contemplated by the Applicant that the present invention will be supplied as a kit 12 whereby a "dry state" sensor 10 will be packaged with a hydration solution 36 sealed in a hydration (activation) container 35. The pH sensor apparatus 10 is packaged and stored "dry" to maintain component stability and minimize component degradation. When desired, the user removes the sensor from the package and submerges the sensor tip in a hydration solution whereby the hydrophilic coating and electrolyte loaded wick (for example, a dry matrix of hygroscopic materials such as hydroxyethylecellulose and sodium chloride) absorbs the solution, creating an electrolytic gel inside the wick and around the reference element 30, which activates the pH sensor.

A typical hydration solution 36 for sensor activation consists of an aqueous, another polar solution, or a conduction fluid which may contain sodium chloride, potassium chloride or other conductive ion formation materials.

Now referring to FIGS. 3-6, the sensor apparatus 10 and 14 consists of an outer tubular member 15 that is usually fabricated by an extrusion or dip coating process using a variety of polymeric materials including polyimide, polyethylene, polypropylene, polyvinyl chloride, polystyrene, ABS, nylon, acetal, polyethylene terephthalate (PET), fluorinated ethylene-propylene (FEP) or polytetrafluoroethylene (PTFE). The outer tubular member 15 generally has an outside diameter in the range of 0.030" to 0.070", and preferably between 0.040" and 0.060". Its wall thickness is typical for its diameter and generally is in the range of 0.005" to 0.020" and preferably between 0.0010" and 0.015". The outer tubular member 15 may include a coating specific for certain applications, e.g. protection from acid environments, dielectric isolation, etc.

Co-linearly 38, coaxially 39, or multi-luminally aligned within the outer tubular member 15 is a first inner tubular member 17 and a second inner tubular member 37 that is also usually fabricated by an extrusion or dip coating process using a variety of polymeric materials including polyimide, polyethylene, polypropylene, polyvinyl chloride, polystyrene, ABS, nylon, acetal, polyethylene terephthalate (PET), fluorinated ethylene-propylene (FEP) or polytetrafluoroethylene (PTFE).

Located within the first inner tubular member 17 is a "dry state" reference wick 19 that is electrically isolated from the antimony metal segment 24 and wire assembly. The reference wick 19 is packaged in a dry, "non-activated" state which functions to maintain component stability and minimize component degradation. In one embodiment (FIG. 3) the sensor apparatus utilizes a multi-lumen design to enclose the antimony metal segment 24 and the reference wick 19, each of the lumens functioning to provide individual tubular members for the antimony metal segment 24 and reference wick 19. In another embodiment (FIG. 4), the reference wick 19 is enclosed within a tubular member that is co-linearly offset with the outer tubular member 15. The reference wick 19, enclosed within an appropriate tubular member, comprises a mesh or fibrous configuration which may incorporate one or more micro-channels (not shown). The dry "non-activated" reference wick 19 can be fabricated from a variety of polymeric based materials. Examples of such materials are polysaccharides, (cotton, regenerated cellulose) polyester, polyethylene, polypropylene, polyvinyl chloride (PVC), polystyrene, ABS, nylon, acetal, polyethylene terephthalate (PET), polytetrafluoroethylene (PTFE), collagen, Hytrel (thermoplastic polyester elastomer), a porous material selected from the group consisting of porous ceramic, metallic or polymeric material, or any material or combination of materials which exhibit a weave, felt or mesh design that facilitates wicking or ion conduction. One example of a preferable material for the reference wick 19 is a polyester fabric mesh. One or more micro-channels could be incorporated into the mesh to facilitate transport of the hydration solution 36. The polymeric based materials of the wick 19 are impregnated with a matrix of hydrophilic and/or hydroscopic materials such as water soluble hydroxyethylcellulose and sodium chloride that when hydrated, becomes an electrolytic gel. One example of the wick 19 that can be used with the sensor 10 is a polysaccharide based gel, 1-10 percent, with a preferred range of 3-5 percent, which is incorporated with a solution of sodium chloride and water. Other materials that can function as the reference wick 19 with a hydration solution 36 include ion carrying gels, hydrogels, and excipients. These gels, hydrogels, and excipients aid in maintaining the stability of the reference element 30.

Located within the second inner tubular member 37 is an antimony metal segment 24 having a surface area 22 at the terminal end. The antimony metal segment 24 is generally 99% pure and free from significant contaminates. The Applicant contends that the antimony metal segment 24 could be replaced with other metallic substances like antimony that exhibit a change in electrical potential when immersed in different pH fluids. Furthermore, other potential materials such as specially formulated polymers, semiconductor technology, Ion Sensitive Field Effect Transistors (ISFETs), optical sensing, capacitive sensing, and nanotechnology could be employed.

The antimony metal segment 24 is engaged at its proximal end to an electrical communication means 26. Typically electrical wire 26 has an internal core comprised of an electrically conductive metallic material that is encased by a nonconductive jacket. The means of engagement typically employs standard soldering technology and can be supported by a variety of means to provide strain relief. The surface 22 of the antimony metal segment 24 defines the distal terminal boundary of the sensor and is the surface that is exposed to liquid or humid gaseous environments.

Located proximally, from a range of 0.5-8.0 centimeters from the distal end of the reference wick 23 and preferably 0.1-3.0 centimeters, and engaging a portion of the reference wick, is a reference element or electrode 30. Said reference element or electrode 30 is primarily composed of a silver core surrounded with a coating of silver chloride. Technology of dipping a silver core in a high temperature bath of silver chloride to produce the silver chloride coating is employed in the present invention. The resulting coating generally is 0.001" to 0.010" in thickness, and preferably 0.002" to 0.005". Reference element 30 is engaged to an electrical communication means 28, e.g. typical wire that extends to the proximal end of the outer tubular member 15 and can terminate in a typical electrical connector (not shown). An expansion plug is located at the proximal end of the tube and is made of a hydrophilic material. When dry, the plug is relatively loose allowing air to escape out the back of the tube during capillary liquid flow. When the liquid comes in contact with the plug, the plug expands and seals the proximal end of the tube preventing any further capillary action and liquid Absorption, which can affect the electrolyte concentration. To initiate hydration and increase the wetability of the reference wick, a hydrophilic and/or hydroscopic coating is applied to the sensor tip. When the hydration solution contacts the reference element, the pH sensor is activated.

The performance of the sensor may be enhanced in some environments by the inclusion of a coating or other surface modification on this distal surface. One example would be a hydrophilic and/or hygroscopic coating to enhance the absorption and retention of moisture on the sensor in humidified gases and aerosols. Materials such as hydrophilic and/or hygroscopic polyurethanes, polyacrylamides, poly(2-hydroxyethyl-methacrylate), other methacrylate copolymers, perfluorinated polymers, polysaccharides, polyvinyl chloride, polyvinyl alcohol and silicones could all be utilized. Examples of surface modifications could include plasma using H2O, Co2 and or N2, RF energy, or radiation either alone or in combination with other chemical depositions or reactions. A plasma treatment followed by grafting of hydrophilic monomers (acrylic acid and acrylamide) in the vapor phase could also be utilized. The coatings and surface modifications either alone, in combination, or with modifications could be utilized as surface enhancements to improve the wet ability and hence the absorption of moisture on the distal sensor tip in humidified gases and aerosol environments.

Positioned proximal to the reference element 30 is a singular or plurality of sodium chloride rods 34 that are positioned in close proximity to the reference wick 19 which dissolves into the hydration solution to retain a stable electrolyte concentration.

Proximal to the sodium chloride rods 34 is the expansion plug 32 generally located near the proximal end of the inner tubular member 17. The expansion plug 32 allows venting of the inner tubular member 17 into the space of the outer tubular member 15, encouraging capillary action and then seals against the inner tubular member 17 after it becomes hydrated.

With the composition of hygroscopic and/or hydrophilic materials of the reference wick 19, the hydroscopic and/or hydrophilic coating on the terminal end, and the proximal location of the expansion plug 32 and sodium chloride rods 34, when the terminal end of the sensor is submerged into the hydration solution 36, the solution 36 enters the terminal end of the reference wick 19 and is transported by capillary action through the reference wick 19 and towards the expansion plug 32.

Now referring specifically to FIG. 6, at the time activation of the sensor is desired, the tip of the sensor apparatus is submerged into a hydration solution 36, whereby the hydrophilic and/or hygroscopic coating and the structure of the reference wick absorbs the fluid, creating an electrolytic gel 20 with and around the reference wick 19 inside inner tubular member 17. The level of the absorbed fluid is influenced by the expansion plug 32 and sodium chloride rods 34 and is designed to at least reach the reference element 30, thereby electrically activating the pH sensor 14. The present invention sensor 10 will become activated within a typical period of approximately 1 to 10 minutes after immersion in the hydration solution 36 and will remain activated throughout its intended use.

FIG. 7 is the present invention sensor 10 being used in an example liquid environment. Sensor apparatus 10 or 14 is shown immersed within a fluid 44 contained in a flask 42. Extending from the sensor 10 or 14 are the antimony metal segment electrical communication means 26 and reference element 30 electrical communication means 28 which are connected to a display/processing means 40. The sensor can provide an immediate reading of the pH level of the fluid 44 or the sensor could be used to monitor pH of the fluid continuously over time to detect changes in the pH.

FIG. 8 is the present invention sensor apparatus 10 are being used in an example humid gaseous environment. Shown in FIG. 8 is pump 46 forcing humid gas 48 through a passageway 47. Sensor apparatus 10 is positioned within the passageway and exposed to the humid gas to provide a means for continuously monitoring the pH of the gas.

FIG. 9 is the present invention sensor being used in an example clinical application. In FIG. 9, sensor apparatus 10 is shown attached to a nasal cannula or intranasal catheter (or a mask) that is positioned on the face of patient 50 so that it is exposed to the patient's exhaled breath either outside the body or in the patient's airway. In this example, the pH of the patient's breath can be continuously monitored. Extending from the sensor apparatus 10 are the antimony metal segment electrical communication means 26 and reference element electrical communication means 28, which are connected to display/processing means 40. The sensor can provide an immediate reading of the pH of the patient's breath or the sensor could be used to measure the pH of the patient's breath for a period of time to monitor and diagnose certain respiratory conditions. Another potential use of the sensor apparatus 10 in clinical applications is to detect the absence of breath, a condition known as sleep apnea.

While the invention has been described in detail and with reference to specific embodiment thereof, it will be apparent to one skilled in the art that various changes and modifications can be made therein without departing from the spirit and scope thereof.

We claim:

1. A controlled activation sensor assembly for monitoring pH or other constituents, comprising:
    a tubular member having a proximal end and a distal end, said tubular member comprised of an outer tubular member and one or more inner tubular members, said outer tubular member co-linearly or coaxially enclosing one or more inner tubular members, said outer tubular member having a terminal end;
    a dry state wick material enclosed within a first inner tubular member, said dry state wick material including a dry matrix of hygroscopic and/or hydrophilic materials, said dry state wick material acting as a capillary tube that facilitates liquid flow;
    a dry state reference electrode, said dry state reference electrode comprising a silver wire terminally coated with a silver chloride coating, said dry state reference electrode enclosed in a proximal position within said dry state wick material and within said first inner tubular member,
    an expansion plug located proximal to said dry state wick and within said inner tubular member, said expansion plug designed to regulate the amount of liquid absorbed and control the electrolyte concentration;
    one or more sodium chloride rods that are positioned in close proximity to the reference wick;
    an antimony metal segment enclosed within said outer tubular member, said outer tubular member electrically isolates said antimony metal segment from said reference electrode;
    said tubular member, said dry state wick, said dry state reference electrode, and said antimony metal forming a non-active sensor; and
    said non-activated sensor designed to become activated upon exposing said distal end to a hydration solution whereby said hydration solution is transported proximally to become retained within a portion of said wick material.

2. The sensor as recited in claim 1, wherein said dry state wick material is selected from the group consisting of fibrous polymeric meshes of polyester, polyimide, polyethylene, polypropylene, polyvinyl chloride, polystyrene, ABS, nylon, delrin, or polyethylene terephthalate (PET), polytetrafluoroethylene (PTFE), polysaccharide, or any combinations thereof.

3. The sensor as recited in claim 1, wherein said dry state wick is a porous material selected from the group consisting of porous ceramic, metallic or polymeric materials.

4. The sensor as recited in claim 1, further comprising one or more sodium chloride rods located proximal to said dry state wick and within said inner tubular member.

5. The sensor as recited in claim 1, further comprising an expansion plug located proximal to said dry state wick and within said inner tubular member.

6. The sensor as recited in claim 1, wherein said hydration solution consists of an aqueous, another polar solution, or a conduction fluid which may contain sodium chloride, potassium chloride or other conductive ion formation materials.

7. The sensor as recited in claim 1, wherein said dry state wick comprises an electrolyte/water based gel when activated.

8. The sensor as recited in claim 1, wherein said dry state wick comprises a conductive polymer when activated.

9. The sensor as recited in claim 1, wherein said dry state reference element comprises a silver element having a silver chloride coating.

10. The sensor as recited in claim 1, further comprising a hygroscopic and/or hydrophilic coating adhered to said distal end.

11. The sensor as recited in claim 1, further comprising an electrical and display means which is in communication with the sensor and processes information obtained from said sensor for presenting a pH reading.

12. A controlled activation sensor for monitoring pH or other constituents, comprising:
    an outer tubular member and an inner tubular member, said outer tubular member co-linearly or coaxially enclosing an inner tubular member, said outer tubular member having a terminal end;
    a dry state wick material located within said inner tubular member, said wick material impregnated with a dry matrix of hydroscopic and/or hydrophilic materials, said wick material including one or more micro-channels, said dry state wick material acting as a capillary tube that facilitates liquid flow;
    a dry state reference electrode, said dry state reference electrode comprising a silver wire terminally coated with silver chloride coating, said dry state reference electrode enclosed in a proximal position within said dry state wick material and within said first inner tubular member;
    one or more sodium chloride rods that are positioned in close proximity to the reference wick;
    an antimony metal segment enclosed within said outer tubular member, said outer tubular member electrically isolates said antimony metal segment from said reference electrode;
    an expansion plug located proximal to said dry state wick and within said inner tubular member, said expansion plug designed to regulate the amount of liquid absorbed and control the electrolyte concentration;
    said controlled activation sensor becoming activated upon exposing said terminal end to a hydration solution whereby said solution facilitates said solution to proceed proximally up said wick and one or more micro-channels to become entrained within said wick material; and
    said sensor assembly being of a small mass such that it functions to cool efficiently and subsequently condenses humid gases in close proximity to said sensor to form a liquid on said terminal end.

13. The sensor as recited in claim 12, wherein said dry state wick material is selected from the group consisting of fibrous polymeric meshes of polyester, polyimide, polyethylene, polypropylene, polyvinyl chloride, polystyrene, ABS, nylon, delrin, or polyethylene terephthalate (PET), polytetrafluoroethylene (PTFE), polysaccharide, or any combinations thereof.

14. The sensor as recited in claim 12, wherein said dry state wick is a porous material selected from the group consisting of porous ceramic, metallic or polymeric materials.

15. The sensor as recited in claim 12, further comprising one or more sodium chloride rods located proximal to said dry state wick and within said inner tubular member.

16. The sensor as recited in claim 12, further comprising an expansion plug located proximal to said dry state wick and within said inner tubular member.

17. The sensor as recited in claim 12, wherein said hydration solution consists of an aqueous, another polar solution, or a conduction fluid which may contain sodium chloride, potassium chloride or other conductive ion formation materials.

18. The sensor as recited in claim 12, wherein said dry state wick comprises an electrolyte/water based gel when activated.

19. The sensor as recited in claim 12, wherein said dry state wick comprises a conductive polymer when activated.

20. The sensor as recited in claim 12, wherein said dry state reference element comprises a silver element having a silver chloride coating.

21. The sensor as recited in claim 12, further comprising a hygroscopic and/or hydrophilic coating adhered to said distal end.

22. The sensor as recited in claim 12, further comprising an electrical and display means which is in communication with the sensor and processes information obtained from said sensor for presenting a pH reading.

23. A controlled activation sensor kit for monitoring pH or other constituents:
    a non-activated sensor, said non-activated sensor comprising:
    an outer tubular member and an inner tubular member, enclosing one or more inner tubular members, said outer tubular member having a terminal end;
    a dry state wick material located within said inner tubular member, said wick material impregnated with a dry matrix of hydroscopic and/or hydrophilic materials, said wick material including one or more micro-channels, said dry state wick material acting as a capillary tube that facilitates liquid flow;
    a dry state reference electrode, said dry state reference electrode comprising a silver wire terminally coated with silver chloride coating, said dry state reference electrode enclosed in a proximal position with said dry state wick material within a first area;
    an expansion plug located proximal to said dry state wick and within said inner tubular member, said expansion plug designed to regulate the amount of liquid absorbed and control the electrolyte concentration;
    one or more sodium chloride rods that are positioned in close proximity to the reference wick;
    an antimony metal segment enclosed within a second area, said outer tubular member electrically isolates said antimony metal segment from said reference electrode;
    a hydration solution stored in a container.

* * * * *